US006228408B1

United States Patent
Van Rijn et al.

(10) Patent No.: US 6,228,408 B1
(45) Date of Patent: *May 8, 2001

(54) ANTIFUNGAL COMPLEXES AND METHOD OF MAKING

(75) Inventors: Ferdinand Theodorus Jozef Van Rijn, Delft; Jacobus Stark, Rotterdam; Edith Magda Lucia Geijp, Pijnacker, all of (NL)

(73) Assignee: DSM Patents and Trademarks (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/369,777

(22) Filed: Aug. 6, 1999

Related U.S. Application Data

(63) Continuation of application No. 09/042,134, filed on Mar. 13, 1998, now Pat. No. 5,997,926.

(30) Foreign Application Priority Data

Mar. 14, 1997 (EP) ................................... 97200764

(51) Int. Cl.⁷ .................. A23B 4/22; A23B 7/16
(52) U.S. Cl. ............. 426/335; 426/44; 426/323; 426/334; 426/580; 426/583; 426/601; 426/634; 426/656
(58) Field of Search ............... 426/334, 44, 323, 426/335, 580, 583, 601, 634, 656

(56) References Cited

U.S. PATENT DOCUMENTS 4,002,741   1/1977   Kulbakh et al. .
5,196,344 * 3/1993   Ruttan ................................ 426/335
5,597,598 * 1/1997   van Rijn et al. ................... 426/335
5,997,926 * 12/1999  van Rijn et al. ................... 426/334

FOREIGN PATENT DOCUMENTS 0 466 038      1/1992   (EP) .
409010288A *   1/1997   (JP) .

OTHER PUBLICATIONS

Maertlbauer et al. "Lehrstuhl fuer Hygiene und Tech. der Milch". Archiv fuer Lebensmittel–hygiene 41 (5) 112–115 (abstract only), 1990.*

Brik, H., "Natamycin", *Analytical Profiles of Drug Substances* 10:513–561 (1981).

De Boer, E., et al., "Sensitivity to natamycin (pimaricin) of fungi isolated in cheese warehouses", *J. of Food Prot.* 40:533–536 (1977).

Daamen, C.B.G. and van den Berg, G., "Prevention of mould growth on cheese by means of natamycin", *Voedingsmiddelentechnologie* 18(2):26–29 (1985).

Maertlbauer et al., "Lehrstuhl fuer Hygiene und Tech. der Milch" Archiv fuer Lebensmittel–hygiene, 41 (5) 112–115, 1990 (Abstract only).

* cited by examiner

Primary Examiner—Helen Pratt
(74) Attorney, Agent, or Firm—Kate H. Murashige

(57) ABSTRACT

A complex comprising natamycin complexed to one or more proteins. Processes for producing the same. Compositions containing the same. Use of the complexes as a preventative antifungi treatment for natural products. A method for preventing the infection of a natural product by fungi, the method comprising treating the natural product with the complex.

14 Claims, 2 Drawing Sheets

ANTIFUNGAL COMPLEXES AND METHOD OF MAKING

Figure 1:
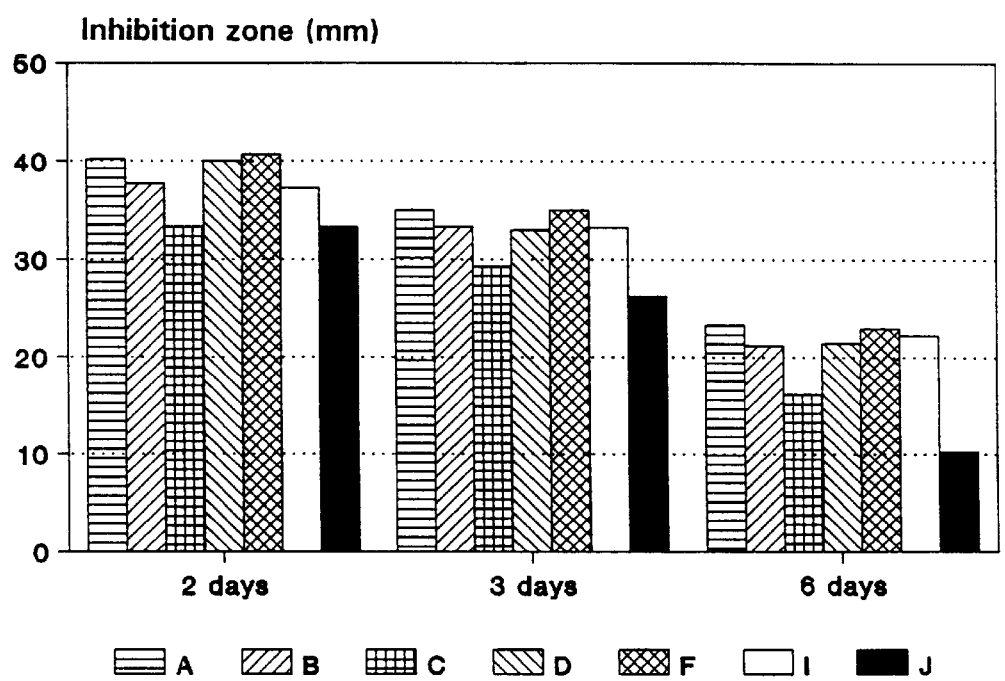

This application is a continuation of application Ser. No. 09/042,134, filed Mar. 13, 1998, now U.S. Pat. No. 5,997,926 which claims benefit of priority to European Application No. 97200764.5 filed Mar. 14, 1997.

The present invention relates to the preparation of compositions which comprise natamycin and the use of such compositions to treat foods such as cheeses and sausages or agricultural products such as fruits, grains and seeds. Also said products treated with compositions of the invention are disclosed.

For more then 20 years natamycin has been used to prevent fungal growth on cheeses and sausages.

Cheeses are treated by immersion in a suspension of natamycin in water or covered by an emulsion of a polymer in water, mostly polyvinyl acetate. Sausages are mainly treated by immersion or by spraycoating with a suspension of natamycin in water. Usually aqueous suspensions for immersion treatments contain 0.1% to 0.2% w/v of natamycin, while polymer emulsions for coating purposes contain 0.01% to 0.05% w/v of natamycin.

These treatments can be highly effective in preventing fungal growth on the surface of cheeses and sausages. However because of the low solubility of natamycin, mould species which are less susceptible to natamycin sometimes are not fully inhibited. Thus some fungal spoilage still may occur. Examples of fungal species which are more tolerant towards natamycin are *Verticilium cinnabarinum, Botrytis cinerea* and Trichophyton species. More tolerant species may also be found among those of the genii Aspergillus, Fusarium and Penicillium. An example of such a species which sometimes causes mould problems in cheese industry is *Penicillium discolour*.

Due to the low solubility of natamycin a food product treated with this antimycotic will be protected against fungal growth for a longer period. only the natamycin which is in solution will be available to exert anti-fungal activity.

Natamycin has a MIC (Minimal Inhibitory Concentration) of less than 10 ppm for most foodborn fungi, while its solubility in water is from 30 to 50 ppm (Brik, H.; "Natamycin" Analytical Profiles of Drug Substances 10, 513–561, (1981)). After many years of continuous use of this antimycotic natamycin-resistant fungi have never been found (De Boer, E.; Stolk-Horsthuis, M.; "Sensitivity to natamycin (pimaricin) of fungi isolated in cheese warehouses" J. of Food Prot. 40, 533–536, (1977)). Under normal conditions natamycin will protect food products such as cheese fully against fungal spoilage for a short period of time. However, sometimes the amount of fungi present in the surroundings is high, for example in a cheese factory, such that the dissolved fraction of natamycin is insufficient to prevent fungal growth on cheese, or the production or storage conditions in factories are particularly favourable for fungal growth. An example of an important factor which enhances fungal growth is an insufficient control of the relative humidity.

In such cases the more tolerant mould species will grow on natamycin treated products.

Spoilage by moulds can cause considerable economic losses and a more efficient antifungal system is necessary to protect food products such as cheese against spoilage by more natamycin-tolerant mould species.

The present invention relates to a process seeking to improve the activity of natamycin towards fungi and to compositions prepared according to said process. In particular such compositions can be useful for combatting moulds and yeasts which are normally relatively less sensitive to the action of natamycin.

In the case of fungi with relatively low susceptibility to natamycin solubilisation and diffusion may have a more limiting effect on its antifungal activity. When a conventional fungicide preparation containing natamycin is employed, at the state of equilibrium the average amount of dissolved natamycin may drop below the effective concentration because elimination will not be adequately compensated by dissolution and diffusion of the antifungal compound.

Modification of the polymorphic form of polyene antifungal compounds, such as natamycin, may also lead to an improved activity of these compounds towards less susceptible species European Patent Application No. 670676, (1995)). Examples of such modified forms are solvates of natamycin, such as the methanol solvate and crystal modifications of natamycin. The activity of polyene fungicides can also be enhanced by converting the compound into an earth alkaline metal salt, such as the calcium and barium salts.

Another method to enhance the activity of polyene fungicides is to first dissolve the antifungal compound in a solvent and then incorporate the dissolved fungicide in an aqueous composition (European Application No. 670676). Examples of suitable solvent systems are lower alcohols such as methanol, ethanol and propanol; glycerol and glycol; methoxy ethanol and ethoxy ethanol; glacial acetic acid and aqueous acid and alkaline solutions; also suitable solubilizers can be used.

These modified polyene antibiotics can also be applied on a carrier by well known methods; e.g. by spray coating techniques using a solution of the antifungal composition on a carrier or by evaporating the solvent from a mixture of a solution of the antifungal and the carrier.

The solution of the antifungal compound may be incorporated into the final composition by adding the solution to a preparation or vice versa.

Enhancing the activity could be achieved by improving the availability of the antifungal compound as a result of improved dissolution (EP 670676). The solubility in water can be increased using alkaline or acidic conditions. The solubility can also be enhanced by using solvents. However it is well known that dissolved natamycin is rapidly decomposed under such conditions (Brik, vide supra). Further dissolved natamycin is known to be less stable compared with the crystal form. Natamycin for instance may be deactivated by decomposition through the action of light or by hydrolysis.

It can be concluded that all known methods to enhance the activity of polyene fungicides by enhancing the vailability leads to a rapid decomposition of the polyene fungicide.

Unexpectedly it has been found that the activity of natamycin towards moulds and yeasts can be markedly enhanced if natamycin is complexed to a suitable compound.

Moreover it has been found that the complexes described in this document are very stable under aqueous conditions, eg. cheese coating or a dipping/spraying solution.

The present invention provides a complex, comprising natamycin complexed to one or more proteins or amino acids, when present in water, does not produce crystals visible at 400×magnification.

Advantageously this complex does not substantially lose activity within 60 days. In general, the ratio of natamycin to the total amount of protein or amino acid is 10,000:1 to 1:10, preferably this ratio is 100:1 to 1:1.

Preferably at least one of the proteins is a milk protein, more preferably a whey protein, casein or caseinate.

The complex can be produced by the following method:
(1) dissolving natamycin in an aqueous liquid by increasing or reducing the pH, such as by using well known methods;
(2) mixing the (dissolved) natamycin with the suitable compound (or complexing agent);
(3) adhering natamycin to the suitable compound by adjusting the pH to the required level using well known methods; and optionally
(4) isolating the complex of natamycin adhered to the suitable compound from the liquid fraction using known methods.

The complex can also be produced using the following method:
(1) dissolving natamycin in a suitable solvent system;
(2) adhering the natamycin to the suitable compound by mixing the dissolved natamycin with that compound; and
(3) optionally isolating the complex of the natamycin adhered to the suitable compound from the liquid fraction using methods known per se. This compound can be present in an aqueous solution or suspension.

The complex of natamycin adhered to a suitable compound can be used for different applications including to prevent fungal infection and growth on natural products e.g. cheeses or sausages.

Before application the formed and optionally purified complex can also be mixed with aqueous systems, such as water or cheese coating, or with other suitable compounds.

Instead of isolating the complex it is also possible to use the complex in the aqueous composition or in the solvent system directly, for example in the application of cheese coating.

The enhanced activity of a composition of the present invention is thought to be due to improved availability of the anti-fungal compound as a result of improved dissolution.

Usually only natamycin which is in solution will be available to exert anti-fungal activity. In the case of a fungicide with a low solubility one of the factors which influences the fungicidal effect is the dissolution of the fungicide. Other important factors are the diffusion of the dissolved fungicide to the side of contamination and the elimination of the dissolved fungicide. Natamycin for instance may be inactivated by decomposition through the action of light or by hydrolysis (Daam en, C. B. G. and Berg, G. van den; "Prevention of mould growth on cheese by means of natamycin" Voedingsmiddelentechnologie, 18 (2), 26–29, (1985)).

Natamycin has a minimal inhibitory concentration (MIC) of less than 10 ppm for most foodborn fungi. As mentioned above the solubility of natamycin in water is from 30 to 50 ppm, which is in most cases enough to prevent fungal growth for a short period of time. Elimination of dissolved natamycin is generally compensated sufficiently in these situations by dissolution of undissolved natamycin and by diffusion of dissolved natamycin to the site of infection.

In the present invention a complex of natamycin adhered to a suitable compound is described. Also methods to produce these complexes are disclosed.

One method to produce the complex of natamycin adhered to a suitable compound is by dissolving the natamycin by increasing or reducing the pH using methods known in the art. Preferably the pH is above 10 or below 4. Examples of suitable aqueous acids are aqueous solutions of HCl, $H_2SO_4$, citric acid and lactic acid. Examples of suitable alkaline solutions are solutions of hydroxides such as NaOH, KOH and $NH_4OH$.

The dissolved natamycin is mixed with the suitable compound, preferably a protein or amino acid. Preferably a food grade proteins is used. Examples of suitable proteins are milk proteins, e.g. whey proteins, caseins and caseinates or other compounds, such as L-glutamine. Also mixtures of different proteins and mixtures of proteins with other compounds such as fats e.g. vegetable and animal fats or oils such as milk fat, butter fat, soya bean oil and sunflower oil can be used. Also compositions or products which contain (mixtures of) these compounds can be used. Examples of such mixtures are cow milk or soya bean milk.

After mixing the dissolved natamycin with the suitable compound, the pH is adjusted between 5 and 9, preferably between 6 and 8. When the suitable compound was not present, natamycin will crystallize. It has been surprisingly found that the presence of the suitable compound may prevent the formation of visible crystals when using a microscope having a magnitude of 400×. It is thought that natamycin and the compound (e.g. milk, proteins) form a complex which is not visible using the microscope at this magnification. Possibly this complex is formed at the surface of the protein. We noted that at high natamycin/protein ratios part of the natamycin did not always form the complex but instead could form crystals.

Another method to produce a complex of natamycin and the suitable compound is by dissolving the natamycin in a suitable solvent system.

Suitable solvent systems are lower alcohols such as methanol, ethanol, propanol, ethylene glycol, propylene glycol and glycerol and mixtures thereof. Further, in a suitable alcoholic solvent, one or more hydroxyl groups may be linked by an ester bond to a fatty acid or linked to another alcohol group by an ether bond. Examples of such solvents are methoxy ethanol and ethoxy ethanol.

In addition solubilisers such as surfactants may be added to the solvent. Examples of suitable solubilizers are sodium lauryl sulphate, dioctyl sulphosuccinate, calcium chloride or surfactants of the non-ionic type, for instance those which are sold under the trade marks Tween, Span, Brij and Myrj.

Adhesion or complex formation between the natamycin and the suitable protein, can be achieved by adding the protein to the solution or vice versa. The protein can already be present in an aqueous environment such as water or milk.

The complex of natamycin and the one or more proteins can be used directly in the desired application or can be processed further. For example the complex can be isolated and/or purified using well known methods. Examples of drying methods to separate the complex from a liquid are filtration, centrifugation, evaporation of the liquid, spray drying, freeze drying and fluid bed drying.

Also under aqueous conditions, eg. in a cheese coating, the complex can be stored over a long period e.g. at least half a year without losing substantial activity.

The purified complex of natamycin and one or more proteins may be used for the treatment of natural products such as foodstuffs or other edible substances e.g. cheeses or sausages, agricultural products e.g. flower bulbs, (kernel) grain and vegetables.

Also the unpurified complex of natamycin and one or more proteins in the aqueous system or in the solvent system may be used for the treatment of said natural products.

Compositions comprising a complex of the invention can be used for the treatment of food and agricultural products according to treatment methods known per se, e.g. dipping or spraying.

The antifungal composition of the invention may be used for treating any natural product prone to mycobacterial infection such as a food or agricultural product. Particularly preferred for use in treatments are emulsions prepared from coating emulsions commonly employed in the food industry. For example for the treatment of cheeses an aqueous polymer emulsion of the polyvinyl acetate type, is which can be used by brushing or with a spray device, may be used. A composition of the invention may also be in the form of an emulsion (e.g. for coating) of the oil-in-water or water-in-oil type. Examples of suitable preparations for treating agricultural products such as fruits are films of polymeric materials such as for example polyolefins, e.g. polyethylene and polypropylene.

The amount of natamycin in a liquid composition for immersion or spraying treatment may be from 0.01% to 2% w/v. Preferably the amount is from 0.01% to 1% w/v. In principle the immersion liquid may be of any kind. When an aqueous system is used, the addition of a surfactant may be of advantage, in particular for treating objects with a hydrophobic surface. Useful surfactants are for example anionic tensides such as sodium lauryl sulphate or polyethylene alkyl ethers such as Cetomacrogol® 1000 or polyoxyethylene ethers e.g. Tween® 60, 61 and 65.

In a coating emulsion according to the invention, the amount of natamycin may be from 0.005% to 2% w/v, preferably from 0.01% to 1% w/v and more preferably from 0.01% to 0.5% w/v.

Legend to the Figures

FIG. 1 gives the inhibition zone (in mm) of *Penicillium discolour* as function of time (days)

Figure 2:
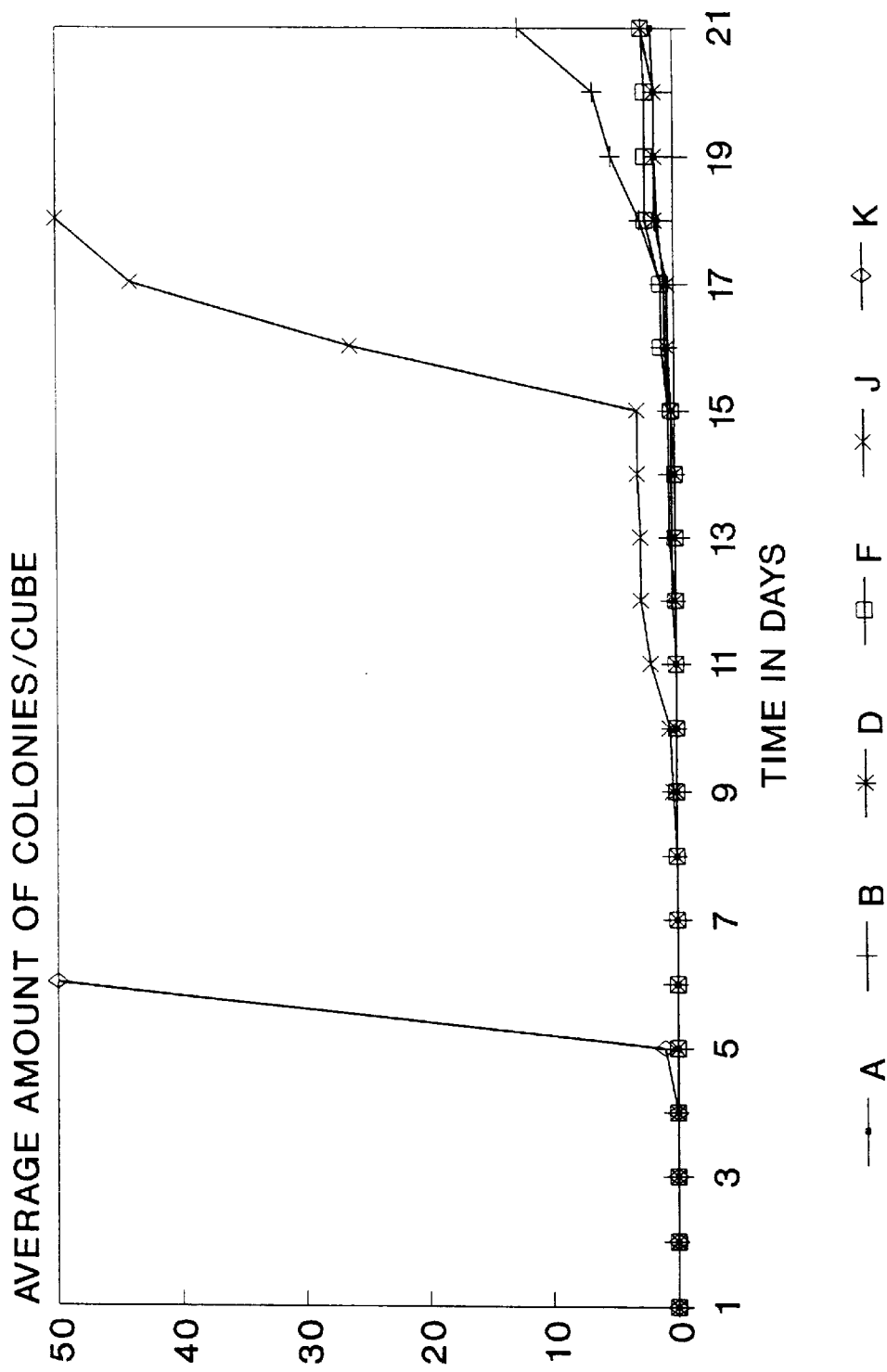

FIG. 2 shows the average amount of colonies/cube as a function of time

The invention will now be described by way of example with reference to the accompanying Examples which should not be regarded as being limiting.

EXAMPLE 1

This example describes a microbiological method for determining the availability of an anti-fungal component from an anti-fungal composition.

Filter paper discs (S&S Antibiotics Test Discs no. 321260 with a diameter of 0.6 cm were loaded with the preparation to be tested. Each disc was loaded with 250 µg of natamycin, i.e. 50 µl of a sample containing 5000 ppm of natamycin was applied to a disc. The discs were then placed on agar which was seeded with *Saccharomyces cerevisiae* ATCC 9763 and incubated at 30° C. for 24 hours. As a reference, discs were freshly loaded with a range of known amounts of natamycin dissolved in aqueous methanol.

The next day, the sample discs were transferred to new petri dishes containing agar seeded with *Saccharomyces cerevisiae*. New discs freshly loaded with a range of known quantities of dissolved natamycin were prepared for use as a reference. The new dishes with the sample discs and the new references were incubated at 30° C. for 24 hours.

The size of the inhibition zone is a measure of the natamycin released from the sample disc. The amount of released natamycin can then be calculated by known methods.

By repeating the procedure, the released natamycin can be measured on a daily basis.

EXAMPLE 2

This example describes the preparation of the natamycin complexes.

1. 0.5 grammes of natamycin was dissolved in 80 ml of water by increasing the pH to 11.5 using NaOH (4N).
2. Suitable compounds for complexing with natamycin were:
   Sodium caseinate (MIPRODAN® 30, MD food) 3.3% (w/w) dissolved in demineralised water (A)
   whey protein (ESPIRION 580, DMV Veghel) 6.6% (w/w) dissolved in demineralised water (B)
   butterfat (Corman)
   soya bean oil (Cargill)
   sunflower oil (Cargill)
   soya drink (Provamel) (C)
   sterilized milk (Campina). (D)
   Also emulsions (500 ml) were prepared by mixing the following (complexing) compounds and incubated for 5 minutes in an Ultra turax T50 (Janke & Kunkel) machine at 8000–9500 rounds per minute:
   demi-water 96.0%, butterfat (Corman) 4% (E)
   demi-water 92.7% (w/w), 3.3% Sodium caseinate (w/w), butterfat 4.0% (w/w). (F)
   demi-water 92.7%, Sodium caseinate 3.3%, soya bean oil 4% (G)
   demi-water 89.4%, whey protein 6.6%, butterfat 4.0% (H)
   demi-water 89.4%, whey protein 6.6%, sunflower oil 4.0% (I)
3. 5.0 ml of the dissolved Sodium caseinate, dissolved whey protein, soya drink, sterilized milk or the prepared emulsions (A–I) were added to 80 ml aliquots of the dissolved natamycin.
   As a control a sample with only natamycin was prepared.
4. The pH of each of the samples was reduced to 5.8 by adding HCl (4N). Demineralised water was added to a total volume of 100 ml per sample.

EXAMPLE 3

This example describes the release of the different natamycin formulations on daily basis. 50 µl of each sample prepared as described in Example 2 (samples A to J) was applied to a disk as described in Example 1. The release of natamycin from the disks was determined for 3 days by the method described in Example 1. The results are presented in Table 1.

TABLE 1

Release of natamycin (µg/disk) on daily basis

| Suitable compounds | Day 1 | Day 2 | Day 3 |
| --- | --- | --- | --- |
| J (control) | 2.5 | 1.8 | 1.7 |
| A | 8.4 | 7.6 | 6.7 |
| B | 7.8 | 5.4 | 5.3 |
| C | 4.2 | 2.3 | 2.2 |
| D | 6.0 | 7.4 | 6.0 |
| E | 2.7 | 2.0 | 2.1 |
| F | 11.3 | 11.6 | 5.5 |
| G | 9.3 | 7.7 | 5.8 |
| H | 7.5 | 6.0 | 4.0 |
| I | 7.8 | 6.0 | 4.1 |

The release rate of most natamycin complexes was considerably higher than the release rate of the control. This means that more natamycin was probably available to inhibit the moulds. As described before only the dissolved natamycin has anti-fungal activity. Only in the case of formulation E (butterfat) the release rate of natamycin is not improved. In the case of formulation C (soya drink) only on the first day was a higher release rate observed.

EXAMPLE 4

This example describes the activity of the natamycin complexes against *Penicillium discolour*, a more tolerant mould which sometimes causes spoilage problems in the cheese industry.

A spore suspension was prepared by scraping the spores from a sporulated culture of *P. discolour* and suspending the spores in sterile water with 0.05% Tween. The freshly prepared spore suspension was mixed with mould agar to a final concentration of $10^2$ spores/ml agar, and agar plates were prepared. In the middle of the plates a hole with a diameter of 5 mm was made. Into the hole 25 μl of the formulations A, B, C, D, F, I and J (from Example 2) was injected. The plates were incubated for 6 days at 24°0 C. After 2, 3 and 6 days the inhibition zones were measured. The results are presented in FIG. 1. FIG. 1 clearly demonstrates that *P. discolour* was inhibited to a greater extent by the new formulations then by natamycin alone.

EXAMPLE 5

This example illustrates the effect of the natamycin complexes towards *Penicillium discolour* on cheese. Compositions A, B, D, F and J were prepared as described in Example 2. 5 ml of each composition was mixed with 45 ml Plasticoat® (an aqueous emulsion of polyvinylacetate supplied by National Starch and Chemicals B.V.) in such a way that coating emulsions were obtained containing 500 ppm of natamycin. Also a coating emulsion without natamycin was prepared as a control (K). The coating compositions were applied to the surface of Gouda cheese according to the following procedure:

A freshly brined wheel of Gouda cheese was first cut horizontally into two parts. Each part was then cut into pieces of 5 by 5 by 5 cm. Only pieces with a flat rind surface were used in the experiment. The pieces were dipped into a bath of melted paraffin at 80° C. in such a way that the rind surface remained free of paraffin, while the other five surfaces were covered by a thin film of paraffin. The rind surface was then inoculated with about $1.9 \times 10^3$ CFU/cm$^2$ of a mixture of spores of three strains of *Penicillium discolour* (CBS numbers: 611.92, 612.92 and 613.92). The inoculation was performed by applying 0.15 ml of a spore suspension containing about $2 \times 10^5$ CFU/ml to the surface of the piece of cheese. The inoculum was evenly spread over the surface by means of a sterile swab, which was saturated with the spore suspension. After standing overnight in closed plastic boxes at about 6° C., the pieces of cheese were treated with the different compositions. For each treatment 4 pieces of cheese were taken. On each piece 0.8 ml of the composition A, B, D, F, J or K was applied and evenly spread over the surface by means of a sterile rectangular piece of plastic of about 2 by 5 cm. After standing for 2 hours at ambient conditions, the pieces of cheese were incubated at 15° C. with a relative humidity of 95%. Every day the number of visible colonies formed on each piece of cheese was determined and the average number per piece was calculated for each treatment. When the number of colonies on a piece of cheese exceeded the value of 50, the piece of cheese was considered to be totally covered with mould. The results are summarized in FIG. 2. The results clearly demonstrate the superiority of the compositions according to the invention over natamycin alone. FIG. 2 demonstrates that the new compositions reduce the amount of colonies on the pieces of cheese considerably. Even after 3 weeks hardly any mould growth was observed, while the control pieces treated with natamycin (J) prevented mould growth only for 15 days.

EXAMPLE 6

This example illustrates the effect of the Sodium caseinate concentration towards the release of the natamycin. A 15% Sodium caseinate solution was prepared by dissolving 15 grammes of Sodium caseinate into 100 ml water. The natamycin complexes prepared were as follows.

1. 0.5 grammes of natamycin was dissolved in 75 ml of water by increasing the pH to 11.5 using NaOH (4N).
2. 25 (L), 20 (M), 15 (N), 10 (O), 5 (P), 1 (Q), 0.5 (R), or 0.1 (S) ml of the dissolved Sodium caseinate (15%) was added to the water.
3. The pH of each of the samples was reduced to 5.8 by adding HCl (4N). Water was added to a total volume of 100 ml per sample.

As a control a sample with only natamycin was prepared (J).

50 μl of each sample (formulations J and L to S) was applied to a disk as described in Example 1. The release of natamycin from the disks was determined for 3 days by the method described in Example 1. The released natamycin of the control sample (J) was found to be 2 microgrammes per day. The released natamycin of compositions L, M, N, O, P and Q was found to be 3.5 (Q) to more than 8 (L) times higher on day 1. On days 2 and 3 the release of these compositions was 2 to 4 times higher than the control (J). The release for compositions R and S was higher on day 1 (5 microgrammes of natamycin). On day 2 and 3 the release of natamycin was comparable with the control (J).

EXAMPLE 7

This example describes the release of natamycin from the sodium caseinate complex "N" (see example 6) in Polyvinyl Acetate (PVA) using the dissolution test. Composition "N" was prepared as described in example 6. Said composition was mixed with Plasticoat®, an aqueous emulsion of PVA supplied by National Starch & Chemical B.V., as follows:

5 ml of composition "N" was mixed with 45 gram of PVA (composition "N-PVA")

each disc (see example 1) was loaded with 50 μl of composition "N-PVA" (containing 25 μg of natamycin)

the discs were dried by incubating for 24 hours at room temperature the discs were placed on agar plates (see example 1) and incubated for 24 hours at 6° C.

the discs were removed from the agar plates and placed on a fresh agar plate, after which the pre-incubated plates were incubated for 24 hours at 30° C.

the amount of released natamycin was calculated as described in example 1.

As a control a sample with only natamycin in PVA was prepared ("PVA-J").

The release of natamycin from the discs was determined for 3 days. The results are presented in table 2.

TABLE 2

Release of natamycin in PVA (μg/disc) on daily basis

| composition | Day 1 | Day 2 | Day 3 |
|---|---|---|---|
| PVA-J | 1.5 | 2.5 | 2.5 |
| PVA-N | 4.0 | 4.5 | 3.0 |

The release rate of composition PVA-N is considerably higher than the release rate of the control. This means that if composition N is added to PVA-coating, also more natamycin is available to inhibit moulds.

EXAMPLE 8

This example describes the isolation and stability of the new natamycin compositions. Composition N was prepared as described in example 6. A powder was produced as follows:

- 2.1 liter of composition N was prepared
- the sample was dried using a spray dryer (Buchi) using well known methods which results in 71 grammes of powder (POW-N)
- the powder composition was stored at 6° C. in closed buckets.

The amount of natamycin after spray drying (14.5%) (w/w) was almost the same as the maximal amount of natamycin which can be expected (15.3%) (w/w) based on the amount of natamycin which was added before spray drying. The new composition is not inactivated by the spray drying process.

The stability of the powder composition was determined by measuring the natamycin content of the powder by HPLC (according to IDF standard 140, International Dairy Federation, 1987) immediately after preparation and after 28 days of storage at 20° C. in darkness. There was no significant change in the natamycin concentration after 28 days of storage. Immediately after production and after 28 days of storage the natamycin concentration was 14.5% (w/w).

The powder composition "POW-N" was dissolved in water and added to PVA to a final concentration of 250 ppm. The stability of natamycin in this new formulation (POW-PVA-N) was determined by measuring the natamycin content immediately after preparation and after 28 days of storage at 15° C. in darkness. In both cases the concentration of natamycin was 250 ppm.

The release of natamycin from formulation "POW-N" immediately after production and after 4 weeks of storage at 6° C. was determined as follows:

- "POW-N" was dissolved in water to a final concentration of 5000 ppm
- each disc (see example 1) was loaded with 50 μl of the dissolved formulation (containing 250 μg of natamycin)
- the discs were placed on agar plates (see example 1) and incubated for 24 hours at 6° C.
- the discs were removed from the agar plates and placed on a fresh agar plate, after which the pre-incubated plates were incubated for 24 hours at 30° C.
- the amount of released natamycin was calculated as described in example 1.

The results are presented in table 3.

The release of natamycin from formulation "POW-PVA-N" immediately after production and after 4 weeks of storage at 15° C. was determined as follows:

- the powder composition "POW-N" was dissolved in water and added to PVA to a final concentration of 500 ppm (POW-PVA-N)
- each disc (see example 1) was loaded with 50 μl of composition "POW-PVA-N" (containing 25 μg of natamycin)
- the discs were dried by incubating for 24 hours at room temperature
- the discs were placed on agar plates (see example 1) and incubated for 24 hours at 6° C.
- the discs were removed from the agar plates and placed on a fresh agar plate, after which the pre-incubated plates were incubated for 24 hours at 30° C.
- the amount of released natamycin was calculated as described in example 1.

The results are presented in table 3.

TABLE 3 release of natamycin (μg/disc) immediately after production and after 4 weeks of storage

| Composition | Fresh | 28 days |
|---|---|---|
| POW-N | 43.0 | 43.0 |
| PVA-POW-N | 3.5 | 3.5 |

Remark: the release from a PVA formulation is always lower, because of the delaying properties of the PVA matrix.

These results clearly demonstrate that the new formulations, when produced as a powder or when formulated in PVA, are stable and remain their improved activity.

EXAMPLE 9

This example illustrates the effect of the new natamycin compositions towards moulds on Edam cheese. The experiment was executed in a cheese factory in which Edam cheese was produced. At the time of the field trial there were mould problems caused by *Penicillium discolor*. This cheese factory was selected to demonstraate the enhanced activity towards less sensitive mould species in practice. Coating compositions were prepared as follows:

1. Coating A was prepared as "POW-PVA-N" (see example 8), the only difference with "POW-PVA-N" was that coating A contains 500 ppm of natamycin.
2. Coating B was a standard Plasticoat® containing 500 ppm of standard natamycin.

96 Edam cheeses of 2.5 kg were produced using well known methods. 48 Cheeses were treated with coating A, 48 cheeses were coated with coating B using well known methods. The cheeses were coated two times (approximately 7 grammes of coating per cheese per treatment). After brining the cheeses were stored for 3 days, after which the dried cheeses were treated with coating for the first time. After 5 days the cheeses were turned. The second treatment was after 8 days. After 11 days the cheeses were turned. The cheeses were stored for ripening under standard conditions (relative humidity of 87%, temperature of 11° C.). 21 Days after production the cheeses were visually examined for mould growth on the surface. On 22 cheeses treated with the standard coating (coating B) mould colonies were observed. On the cheeses treated with the new formulation (coating A) only on 3 cheeses mould colonies were observed. These results demonstrate that the new composition is also more effective in combatting moulds on Edam cheese produced and stored in a cheese factory.

What is claimed is:

1. An isolated antifungal complex comprising natamycin complexed to proteins and/or amino acids, wherein the amounts of natamycin and proteins and/or amino acids, when present in water, do not produce crystals visible at 400×magnification.

2. A complex according to claim 1, which when present in water does not substantially lose activity within 60 days.

3. A complex according to claim 1 wherein the ratio of natamycin to the total amount of protein or amino acid is 10,000:1 to 1:10.

4. A complex according to claim 3 wherein the ratio of natamycin to the total amount of protein or amino acid is 100:1 to 1:1.

5. A complex according to claim 1 wherein at least one of the proteins is a milk protein.

6. A complex according to claim 5 wherein the milk protein comprises a whey protein, casein or caseinate.

7. A composition comprising a complex according to claim 1 and a fat or oil.

8. A composition according to claim 7 wherein at least one of the proteins present in the complex and the fat, oil or both originate from milk.

9. A composition according to claim 8 wherein the milk is cow milk or soy milk.

10. An antifungal coating for a food product comprising a complex as claimed in claim 1 or a composition as claimed in claim 7 in an antifungal effective amount.

11. A process for preparing a complex as defined in claim 1 the process comprising:

dissolving natamycin in a solvent;

mixing the dissolved natamycin with one or more proteins; and optionally isolating the complex formed.

12. A process according to claim 11 wherein the solvent is an aqueous liquid and dissolution of the natamycin is achieved by reducing or increasing the pH.

13. A process according to claim 12 wherein the complex is formed by adjusting the pH of the mixture of dissolved natamycin and protein to between 5 and 9.

14. A process according to claim 11 wherein the solvent is an organic solvent and the complex is formed in this solvent or a liquid comprising this solvent.

* * * * *